United States Patent [19]

Herlihy

[11] Patent Number: 4,746,322

[45] Date of Patent: May 24, 1988

[54] HAIR DYE COMPOSITION AND PROCESS FOR USING THE SAME

[75] Inventor: Walter C. Herlihy, Watertown, Mass.

[73] Assignee: Repligen Corporation, Cambridge, Mass.

[21] Appl. No.: 52,172

[22] Filed: May 11, 1987

Related U.S. Application Data

[63] Continuation of Ser. No. 828,129, Feb. 11, 1986, abandoned, which is a continuation-in-part of Ser. No. 664,113, Oct. 22, 1984, abandoned, which is a continuation-in-part of Ser. No. 598,466, Apr. 9, 1984, abandoned.

[51] Int. Cl.$^4$ ............................................. A61K 7/13
[52] U.S. Cl. .................................... 8/405; 8/406; 8/407; 8/412; 8/428
[58] Field of Search .................. 8/405, 406, 407, 412, 8/428

[56] References Cited

U.S. PATENT DOCUMENTS

| 3,653,797 | 4/1972 | Reiss et al. | 8/405 |
| 3,925,008 | 12/1975 | Makino et al. | 252/102 |
| 3,993,436 | 11/1976 | Fujinuma | 424/71 |
| 4,021,538 | 5/1977 | Yu et al. | 424/60 |
| 4,312,813 | 1/1982 | Lindemann et al. | 206/401 |
| 4,390,341 | 6/1983 | Jacobs | 8/405 |

FOREIGN PATENT DOCUMENTS

| 2455376 | 6/1975 | Fed. Rep. of Germany | 8/405 |
| 0032132 | 3/1978 | Japan | 8/405 |
| 0104741 | 9/1978 | Japan | 8/414 |
| 0110337 | 8/1979 | Japan | 8/405 |

OTHER PUBLICATIONS

*The Merck Index*, 10th ed., 1983 (7897).
*Cosmetics Science and Technology*, 2nd ed., vol. 2, p. 298 (1972).
Crebelli, R. et al. (1981) "Mutagenicity of Commercial p-Phenylenediamine and of an Oxidation Mixture of p-Phenylenediamine and Resorcinol in *Salmonella typhimurium* TA98" Fd. Cosmet. Toxicol. 19:79-84.

*Primary Examiner*—Albert T. Meyers
*Assistant Examiner*—John M. Kilcoyne
*Attorney, Agent, or Firm*—Roman Saliwanchik; David R. Saliwanchik

[57] ABSTRACT

The subject invention concerns novel dye compositions and a process for dyeing keratinous fibers, for example, hair, to give a pleasing and stable colored product. The dye composition is a novel combination of three elements to give a dye that, unexpectedly, has highly desirable dyeing properties. This unique combination comprises (1) a suitable organic compound to assist dye dispersion, (2) dye precursors including dopamine, D-dopa, L-dopa, D,L-dopa, or analogs thereof, and (3) iodate or periodate. Desired color variations can be obtained by the use of appropriate color modifiers.

25 Claims, No Drawings

HAIR DYE COMPOSITION AND PROCESS FOR USING THE SAME

CROSS REFERENCE TO RELATED APPLICATION

This application is a continuation of application Ser. No. 828,129 filed 2/11/86 abandoned which is a continuation-in-part of application Ser. No. 664,113 filed Oct. 22, 1984 abandoned which is a continuation-in-part of application Ser. No. 598,466 filed 4/9/84 abandoned.

BACKGROUND OF THE INVENTION

In the past thirty years a variety of chemical systems for dyeing hair have been developed. The most commercially successful of these has utilized phenylenediamine combined with various couplers and modifiers with hydrogen peroxide as the oxidant. Although this system covers gray well it suffers from three problems: phenylenediamine is a known sensitizer; the hair is damaged by repeated exposure to alkaline peroxide; and the color produced may fade over time to an off shade. Furthermore, p-phenylenediamine is oxidized in the presence of resorcinol by hydrogen peroxide to a mutagen that is percutaneously absorbed. (See: Crebelli, R., Conti, L., Carere, A. and Zito, A. [1981] "Mutagenicity of Commercial p-Phenylenediamine and of an Oxidation Mixture of p-Phenylenediamine and Resorcinol in *Salmonella typhimurium* TA98" Fd. Cosmet. Toxicol. 19: 79–84.

Related prior art U.S. Pat. No. 4,021,538 concerns a "Method for Producing Pigmentation in Hair or Skin" by use of esters of dopa because of their solubility in both water and lipid solvents. U.S. Pat. No. 4,390,341 concerns a composition for coloring hair or skin which employs, inter alia, acylated dopamine or acylated tyrosine derivatives and omega amino acids. The compositions and processes of the subject invention are neither disclosed nor suggested by known prior art procedures.

At this time in the hair dyeing art it is clear that a need exists for an effective dye composition to change gray hair to a pleasing black, brown or other color. Such a dye composition desirably should be non-mutagenic, non-sensitizing, do minimal to no damage to the hair and skin, and impart a desired color that is stable to repeated washings and weathering. The novel hair dye composition and dyeing process of the subject invention is a distinct improvement over commercially-available hair dyes and processes for using the same.

BRIEF SUMMARY OF THE INVENTION

The subject invention combines, for the first time in hair dyeing art, three elements to give a dye that, unexpectedly, has highly desirable dyeing properties. This unique combination comprises (1) a suitable organic compound to assist dye dispersion, (2) dye precursors including dopamine, D-dopa, L-dopa, D,L-dopa, or suitable analogs thereof, and (3) iodate or periodate. The result of this combination of dyeing elements is manifested by pleasing and stable colors imparted to hair and other keratinous fibers. For example, gray hair is dyed to a pleasing and stable red, brown, or black color. Advantageously, the dyeing agent is non-sensitizing and non-mutagenic. In addition, this melanin-like dye confers several surprising advantageous properties to the hair. There is minimal or no damage to the hair and no dyeing of the skin. The color is stable to washing; however, after a large number of washings (e.g., 20), or after a permanent, the color is observed to fade "on shade," e.g., to a lighter tone of the same color. Thus this process avoids the red or green overtones which are often observed after repeated washing or perming of hair colored with commercially available phenylenediamine-based dyes.

Another unforeseen advantageous property of the subject invention is protection against damage by ultraviolet light. Irradiation of gray hair or gray hair which had been dyed with a commercial dye showed marked damage; whereas gray hair dyed with the method described herein is protected from UV damage.

DETAILED DESCRIPTION OF THE INVENTION

The unique dyeing combination of the subject invention comprises (1) a suitable organic compound to assist dye dispersion; (2) dye precursors including dopamine, D-dopa, L-dopa, D,L-dopa, or suitable analogs thereof, and (3) iodate or periodate.

A suitable organic compound to assist dye dispersion in the subject dye composition is one that is compatible with the dye precursor and that will not react with the oxidant. Examples of suitable organic compounds are selected from the group consisting of phenols, comprising thymol (2-isopropyl 5-methyl phenol); ketone (5–10C), comprising acetophenone, 4-ethyl acetophenone, cyclohexanone, 2,4-dimethyl acetophenone, 3,5-dimethyl cyclohexanone, and 4-methyl cyclohexanone; esters (5–10C), comprising ethylbenzoate, benzyl acetate, benzyl propionate and benzyl butyrate; alcohols, comprising (a) carbocyclic alcohols (5–10C), comprising cyclohexanol, 2-methyl cyclohexanol, (b) heterocyclic alcohol, comprising furfuryl alcohol, (c) aliphatic alcohols (5–8C), comprising hexanol and 2-methyl-1-pentanol, and (d) aryl alkanols, comprising benzyl alcohol, $\alpha,\alpha$,dimethyl benzyl alcohol, $\alpha$-propyl benzyl alcohol, DL-$\alpha$methyl benzyl alcohol, 2-benzyloxyethanol, 2-benzyloxypropanol, 2-benzyloxybutanol, and ethylene glycol phenyl ether; lactones, comprising butyrolactone; 1,2-propylene glycol carbonate; ethylene carbonate; tetramethylene sulfone; butadiene sulfone; tetrahydro thiophene dioxide; 1-substituted azacycloalkane-2-ones, comprising 1-n-dodecylazacycloheptan-2-one; and ethylene glycol sulfite. The suitable organic compound may be present at a concentration of 0.1–30 wt/vol %, and be a mixture of two or more compatible compounds. It should be noted that the above compounds act as dye dispersants. In earlier work on this invention it was believed that the compounds used were facilitating the penetration of the dye into the hair shaft. Subsequent tests showed that the dye was dispersed on the hair shaft with little to no penetration into the hair shaft.

The second key element in the dyeing combination of the subject invention is the use of an acceptable dye precursor, for example, dopamine, D-dopa, L-dopa, D,L-dopa, or suitable analogs thereof, at a concentration of about 1 to about 100 mg/ml (0.1 to about 10 wt/vol %), preferably about 5 to about 25 mg/ml (0.5 to about 2.5 wt/vol %), to the dye composition. The dye precursor, which can be a mixture of two or more compatible compounds, can be shown by the formula:

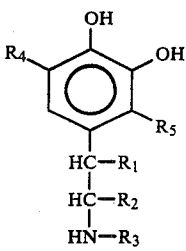

wherein $R_1$, $R_2$ can be the same or different and are: H, alkyl (1–4C), $NH_2$, OH, COOR' (R' is alkyl 1–4C or H), $CONH_2$, halogen (Cl, Br, I, F), OR'' (R'' is alkyl 1–4C), $CH_2OH$, $CH_2NH_2$, or CONR'R'' wherein R' and R'' can be the same or different;

$R_3$ is H or alkyl (1–4C) or COR'';

$R_4$, $R_5$ can be the same or different and are: H, alkyl (1–4C), $NH_2$, OH, COOH, $CONH_2$, halogen, OR'', $NO_2$, $SO_3$, NHR'', NR''R''', $CH_2OH$, or $CH_2NH_2$.

Preferred dye precursors can be shown by the formula

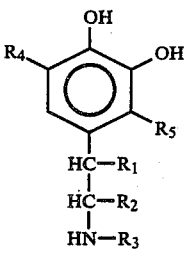

wherein $R_1$, $R_2$ can be the same or different and are: H, $CH_3$, $C_2H_5$, OH, or halogen;

$R_3$ is H, $CH_3$, or $C_2H_5$;

$R_4$, $R_5$ can be the same or different and are as defined previously.

The most preferred dye precursor is dopamine, where in the above formula $R_1=R_2=R_3=R_4=R_5=H$.

Examples of suitable analogs of dopamine, D-dopa, L-dopa, or D,L-dopa are 2-methyldopamine, 5-methyldopamine, or α-(aminomethyl)-3,4-dihydroxybenzyl alcohol. A wider variety of hair colors can be obtained, if desired, by use of dopamine, D-dopa, L-dopa, D,L-dopa, or a suitable analog as defined herein, in conjunction with a color modifier. Such a color modifier, at a concentration of about 0.1 to about 10 mg/ml (0.01 to about 1 wt/vol %) of the dye composition, can be, for example, 4-methylcatechol, 3,4-dihydroxybenzoic acid, 3,4-dihydroxybenzaldehyde, 4-bromocatechol, catechol, 4-methoxycatechol, and the like; or substituted phenols or anilines, for example m-aminophenol, resorcinol, and the like; a thiol such as a cysteine, glutathione or mercaptoacetic acid; or an amino acid such as lysine. The color modifier can be a mixture of two or more compatible compounds.

The third key element is an iodate or periodate oxidizer at a concentration of about 1 to about 50 mg/ml (0.1 to about 5.0 wt/vol %). Though the sodium salt form is preferred, any alkali metal or alkaline earth metal salt of iodate or periodate can be used.

If desired, a thickening agent can be incorporated into the dyeing combination to minimize dripping from the hair. Suitable thickeners include water-soluble resins and gums, for example, carrageenan, guar gum, locust bean gum, and the like; also polymers, such as Carbopol 934 (BF Goodrich Chemical Group, Cleveland, OH), polyvinyl alcohol, and the like; or inorganic materials, for example, Veegum (Vanderbilt Company, Norwalk, CN), nonoxynol-4, nonoxynol-9 (Heterene Chemical Co., Peterson, NJ) or combinations of nonoxynols, and the like. A particularly useful thickening agent is polyethylene glycol-150 distearate (PEG-150 distearate) (Heterene). For example, a 10% solution of PEG-150 distearate is compatible with the dyeing reaction and gives a commercially useful thickened product. Thickening agents can be used in a variety of combinations. The thickener can be present at about 0.1 to about 25% by weight, relative to the total weight of the dye composition.

Upon contacting gray hair with a dye composition comprising an organic compound to assist dye dispersion, dopamine, D-dopa, L-dopa, D,L-dopa, or a suitable analog, and an oxidizing agent, at a pH of 3 to 7 there is obtained hair having a pleasing stable black color. Other colors can be obtained by use of color modifiers and persulfate, as disclosed herein. When a brownish color is desired for the gray hair, then the addition of a persulfate, for example, potassium persulfate at a concentration of about 0.1 to about 20 mg/ml (0.01 to about 2.0 wt/vol %), preferably about 1 to about 5 mg/ml (0.1 to about 0.5 wt/vol %), to the dye composition, can be added.

When an organic compound or color modifier, defined above, is not readily soluble in aqueous solution, it can be solubilized with up to about 50% of an organic solvent, for example, propanol, ethanol, isopropyl alcohol, and the like. These solubilizing solvents are not suitable for use to assist dye dispersion.

The pH of the dye composition should be from about 3 to about 7.0. Standard buffers and acidifying agents can be used to maintain the pH within this range by procedures well known in the hair dye art.

The dyeing process is enhanced at temperatures above room temperature. For example, better dyeing is realized at 35° C. than at 20° C. Higher temperatures can be achieved by a variety of methods, including covering the head with a plastic cap during the dyeing reaction; warming of the dye precursor and oxidant solutions before application, either with an external device or with an exothermic reaction initiated by mixing of, for example, the precursor and oxidant solutions; with an infrared lamp; or by other means well known in the hair dyeing art.

Anionic, cationic, non-ionic or amphoteric water-soluble surface-active agents also can be included in the dye composition. Surface-active agents that can be used are alkylbenzenesulfonates, alkylnaphthalenesulfonates, sulfates, ether-sulfates, and sulfonates of fatty alcohols, quaternary ammonium salts, such as trimethylacetylammonium bromide and cetylpyridinium bromide, diethanolamides of fatty acids, and polyoxyethyleneated or polyglycerolated acids, alcohols or alkylphenols. The surface-active agents are preferably present in the dye composition in a proportion of about 0.1 to about 15% by weight.

Advantageously, a stabilizer can be added to the dye composition if the dopamine dye precursor is in solution. A suitable stabilizer is the reducing agent sodium metabisulfite at a concentration of 1 to about 5 mM (0.1 to about 1 wt/vol %). Other reducing agents such as sodium sulfite, and the like, can be used.

The subject dye composition can be used in various forms, for example, liquid, cream, gel or an aerosol, or in any other form that is suitable for dyeing hair and other keratinous fibers.

Following are examples that illustrate products of the invention and procedures, including the best mode, for practicing the invention. These examples should not be construed as limiting. All percentages are by weight and all solvent mixture proportions are by volume unless otherwise noted.

EXAMPLE 1

Dyeing Gray Hair to Black

Gray hair is contacted with a 12% solution of isopropyl alcohol comprised of dopamine at a concentration of about 5 to about 25 mg/ml (0.5 to about 2.5 wt/vol %), about 10% of ethylene glycol phenyl ether, and sodium periodate at a concentration of about 2 to about 10 mg/ml (0.2 to about 1.0 wt/vol %). The dyeing process proceeds for about 20 to about 60 min, after which the dyed hair is rinsed. The hair now has a pleasing black color.

EXAMPLE 2

Dyeing Gray Hair to Auburn

Gray hair is contacted with an aqueous solution comprised of dopamine at a concentration of about 2 to about 10 mg/ml (0.2 to about 1.0 wt/vol %), catechol at a concentration of about 0.4 to about 2 mg/ml (0.04 to about 0.2 wt/vol %), about 2 to about 4% of benzyl alcohol, the known thickener carrageenan at about 0.5 to about 5% by weight, sodium iodate at a concentration of about 1 to about 5 mg/ml (0.1 to about 0.5 wt/vol %) and ammonium persulfate at a concentration of about 1 to about 5 mg/ml (0.1 to about 0.5 wt/vol %). The process proceeds for about 20 to about 60 min, after which the dyed hair is rinsed. The hair now has a pleasing auburn color.

EXAMPLE 3

Dyeing Gray Hair to Black

Gray hair is contacted with a 10% solution of isopropyl alcohol comprised of dopamine at a concentration of about 5 to about 25 mg/ml (0.5 to about 2.5 wt/vol %), about 1 to about 2% of thymol, sodium iodate at a concentration of about 2 to about 10 mg/ml (0.2 to about 1.0 wt/vol %), and ammonium persulfate at a concentration of about 0.5 mg/ml (0.05 wt/vol %). The process proceeds for about 20 to about 60 min, after which the dyed hair is rinsed. The hair now has a pleasing black color.

EXAMPLE 4

Dyeing Gray Hair to Brown

Gray hair is contacted with an aqueous solution comprised of D,L-dopa or dopamine, at a concentration of about 5 to about 25 mg/ml (0.5 to about 2.5 wt/vol %), 4-methyl catechol in a concentration of about 2 to about 10 mg/ml (0.2 to about 1.0 wt/vol %), about 2 to about 4% of benzyl alcohol, the known thickener carrageenan at about 0.5 to about 5% by weight and sodium iodate at a concentration of about 2 to about 10 mg/ml (0.2 to about 1.0 wt/vol %). The process proceeds for about 20 to about 60 min, after which the dyed hair is rinsed. The hair now has a pleasing brown color.

EXAMPLE 5

Dyeing Gray Hair to Brown

Upon adding potassium persulfate to the dye composition of Example 1, at a concentration of about 1 to about 5 mg/ml (0.1 to about 0.5 wt/vol %) of potassium persulfate to the dye composition, there is obtained hair with a brownish color.

EXAMPLE 6

Dyeing Gray Hair to a Red-Orange Color

Gray hair is contacted with an aqueous solution comprised of dopamine at a concentration of about 5 to about 10 mg/ml (0.5 to about 1.0 wt/vol %), cysteine at a concentration of about 5 to about 10 mg/ml (0.5 to about 1.0 wt/vol %), about 4% benzyl alcohol, about 1 mg/ml (0.1 wt/vol %) ammonium persulfate and about 2 to about 5 mg/ml (0.2 to about 0.5 wt/vol %) sodium iodate. The dyeing reaction proceeds for about 20 to about 60 min, after which the hair is rinsed. The hair has a red-orange color.

EXAMPLE 7

Upon substituting white hair for the gray hair in Examples 1 or 3, the resulting hair has a pleasing black color.

EXAMPLE 8

Upon substituting white hair for the gray hair in Examples 4 or 5, the resulting hair has a brownish color.

EXAMPLE 9

Variously colored hair and other keratinous fibers can be substituted for gray or white hair in the process as disclosed herein to achieve a variety of pleasing and stable colors.

EXAMPLE 10

Upon substituting D-dopa or L-dopa for D,L-dopa in Example 4, there is obtained hair having a pleasing brown color.

EXAMPLE 11

Upon substituting white hair for the gray hair in Example 2, the resulting hair has an auburn color.

EXAMPLE 12

Gray hair is contacted with an aqueous solution of 10% polyethylene glycol-150 distearate, 5 mg/ml (0.5 wt/vol %) dopamine hydrochloride, 22 mg/ml (2.2 wt/vol %) sodium iodate and 20% ethylene carbonate. The scalp is covered with a plastic cap and the reaction is allowed to proceed for about 20 to about 60 min, after which the hair is rinsed. The hair now has a pleasing black color.

EXAMPLE 13

Gray hair is contacted with an aqueous solution of 10% polyethylene glycol-150 distearate, 4 mg/ml (0.4 wt/vol %) dopamine hydrochloride, 0.4 mg/ml (0.04 wt/vol %) lysine hydrochloride, 20 mg/ml (2.0 wt/vol %) sodium iodate and 20% propylene carbonate. The scalp is covered with a plastic cap and the reaction is allowed to proceed for about 20 to about 60 min, after which the hair is rinsed. The hair now has a pleasing brown color.

EXAMPLE 14

Oriental gray hair is contacted with an aqueous solution containing 5 mg/ml (0.5 wt/vol %) dopamine hydrochloride, 11 mg/ml (1.1 wt/vol %) sodium iodate and 30% butadiene sulfone. The scalp is covered with a plastic cap and the reaction is allowed to proceed for about 20 to about 60 min, after which the hair is rinsed. The hair now has a pleasing black color.

I claim:

1. An aqueous dye composition for dyeing hair which does not dye the skin comprising:
   (1) at least one water soluble dye precursor of the formula

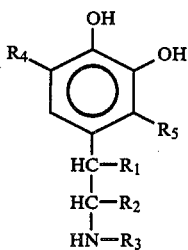

wherein
   $R_1$, $R_2$ can be the same or different and are:
      H, alkyl or 1–4C, $NH_2$, OH, COOR' wherein R' is alkyl of 1–4C or H, $CONH_2$, halogen, OR" wherein R" is alkyl of 1–4C, $CH_2OH$, $CH_2NH_2$, CONR'R" wherein R' and R" can be the same or different;
   $R_3$ is H or alkyl of 1–4C or COR";
   $R_4$, $R_5$ can be the same or different and are:
      H, alkyl of 1–4C, $NH_2$, OH, COOH, $CONH_2$, halogen, OR", $NO_2$, $SO_3$, HNR", or NR"R";
   (2) an alkali metal or alkaline earth metal salt of iodate or periodate;
   (3) at least one organic dye dispersing agent that is compatible with the dye precursor used and will not react with the iodate or periodate oxidant; and
   (4) water.

2. A dye composition, according to claim 1, wherein said dye precursor has the formula

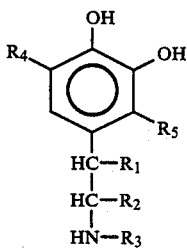

wherein
   $R_1$, $R_2$ can be the same or different and are:
      H, $CH_3$, $C_2H_5$, OH, or halogen;
   $R_3$ is H, $CH_3$ or $C_2H_5$;
   $R_4$, $R_5$ can be the same or different and are as defined in claim 1.

3. A dye composition, according to claim 1, wherein said dye precursor is dopamine, D-dopa, L-dopa, or D,L-dopa.

4. A dye composition, according to claim 1, wherein said dye dispersing agent is selected from the group consisting of 2-isopropyl 5-methyl phenol, acetophenone, 4-ethyl acetophenone, cyclohexanone, 2,4-dimethyl acetophenone, 3,5-dimethyl cyclohexanone, 4-methyl cyclohexanone, ethylbenzoate, benzyl acetate, benzyl propionate, benzyl butyrate, cyclohexanol, 2-methyl cyclohexanol, furfuryl alcohol, hexanol, 2-methyl-1-pentanol, benzyl alcohol, $\alpha,\alpha$,dimethyl benzyl alcohol, $\alpha$-propyl benzyl alcohol, DL-$\alpha$ methyl benzyl alcohol, 2-benzyloxyethanol, 2-benzyloxypropanol, 2-benzyloxybutanol, ethylene glycol phenyl ether, butyrolactone, 1,2-propylene glycol carbonate, ethylene carbonate, tetramethylene sulfone, butadiene sulfone, tetrahydro thiophene dioxide, 1-n-dodecylazacycloheptan-2-one, and ethylene glycol sulfite.

5. A dye composition, according to claim 1, wherein said hair is gray or white hair.

6. A dye composition, according to claim 1, wherein said dye dispersing agent is present at a concentration of about 0.1 to about 30 wt/vol%; said dye precursor is at a concentration of about 0.1 to about 10 wt/vol% to the dye composition; and said alkali metal or alkaline earth metal salt of iodate or periodate is at a concentration of about 0.1 to about 5 wt/vol%.

7. A dye composition, according to claim 1, wherein a thickener is present to minimize dripping from the hair.

8. A dye composition, according to claim 7, wherein said thickener is polyethylene glycol-150 distearate.

9. A dye composition, according to claim 1, wherein a color modifier, or a mixture thereof, selected from the group consisting of 4-methylcatechol, 3,4-dihydroxybenzoic acid, 3,4-dihydroxybenzaldehyde, 4-bromocatechol, catechol, 4-methoxycatechol, m-aminophenol, resorcinal, cysteine, glutathione, mercaptoacetic acid, and lysine is present.

10. A dye composition, according to claim 9, wherein said color modifier is catechol or cysteine.

11. A dye composition, according to claim 1, wherein potassium or ammonium persulfate is present.

12. A dye composition, according to claim 1, wherein a stabilizer is present if the dopamine dye precursor is in solution.

13. A dye composition, according to claim 1, wherein said dye dispersing agent is benzyl alcohol.

14. A dye composition, according to claim 1, wherein said dye dispersing agent is ethylene carbonate.

15. A process for dyeing hair which does not dye the skin and which comprises contacting hair with a dye composition comprising:
   (1) at least one water soluble dye precursor of the formula

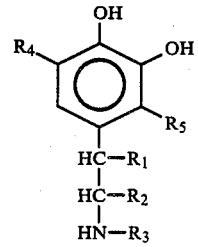

wherein

R$_1$, R$_2$ can be the same or different and are:
  H, alkyl of 1–4C, NH$_2$, OH, COOR' wherein R' is alkyl of 1–4C or H, CONH$_2$, halogen, OR'' wherein R'' is alkyl of 1–4C, CH$_2$OH, CH$_2$NH$_2$, CONR'R'' wherein R' and R'' can be the same or different;

R$_3$ is H or alkyl or 1–4C or COR'';

R$_4$, R$_5$ can be the same or different and are:
  H, alkyl of 1–4C, NH$_2$, OH, COOH, CONH$_2$, halogen, OR'', NO$_2$, SO$_3$, HNR'', or NR''R'';

(2) an alkali metal or alkaline earth metal salt of iodate or periodate;

(3) at least one organic dye dispersing agent that is compatible with the dye precursor used and will not react with the iodate or periodate oxidant; and (4) water for about 20 min to about 60 min, and rinsing the dyed hair.

16. A process, according to claim 15, wherein said dye dispersing agent is selected from the group consisting of 2-isopropyl 5-methyl phenol, acetophenone, 4-ethyl acetophenone, cyclohexanone, 2,4-dimethyl acetophenone, 3,5-dimethyl cyclohexanone, 4-methyl cyclohexanone, ethylbenzoate, benzyl acetate, benzyl propionate, benzyl butyrate, cyclohexanol, 2-methyl cyclohexanol, furfuryl alcohol, hexanol, 2-methyl-1-pentanol, benzyl alcohol, α,α,dimethyl benzyl alcohol, α-propyl benzyl alcohol, DL-α methyl benzyl alcohol, 2-benzyloxyethanol, 2-benzyloxypropanol, 2-benzyloxybutanol, ethylene glycol phenyl ether, butyrolactone, 1,2-propylene glycol carbonate, ethylene carbonate, tetramethylene sulfone, butadiene sulfone, tetrahydro thiophene dioxide, 1-n-dodecylazacycloheptan-2-one, and ethylene glycol sulfite.

17. A process, according to claim 15, wherein said dye composition comprises
  (1) said dye precursor at a concentration of about 0.1 to about 10 wt/vol% to the dye composition;
  (2) said alkali metal or alkaline earth metal salt of an iodate or periodate at a concentration of about 0.1 to about 5 wt/vol%; and
  (3) said dye dispersing agent at a concentration of about 0.1 to about 30 wt/vol%.

18. A process, according to claim 15, wherein said dye precursor is dopamine, D-dopa, L-dopa, or D,L-dopa.

19. A process, according to claim 15, wherein a thickener to minimize dripping from the hair is added to the dye composition.

20. A process, according to claim 19, wherein said thickener is polyethylene glycol-150 distearate.

21. A process, according to claim 15, wherein a color modifier, or a mixture thereof, selected from the group consisting of 4-methylcatechol, 3,4-dihydroxybenzoic acid, 3,4-dihydroxybenzaldehyde, 4-bromocatechol, catechol, 4-methoxycatechol, m-aminophenol, resorcinol, cysteine, glutathione, mercaptoacetic acid, and lysine is added to the dye composition.

22. A process, according to claim 21, wherein said color modifier is catechol or cysteine.

23. A process, according to claim 15, wherein a stabilizer is added to the dye composition if the dopamine dye precursor is in solution.

24. A process, according to claim 15, wherein said dye dispersing agent is benzyl alcohol.

25. A process, according to claim 15, wherein said dye dispersing agent is ethylene carbonate.

* * * * *

UNITED STATES PATENT AND TRADEMARK OFFICE
CERTIFICATE OF CORRECTION

PATENT NO. : 4,746,322
DATED : May 24, 1988
INVENTOR(S) : Walter C. Herlihy

It is certified that error appears in the above-identified patent and that said Letters Patent are hereby corrected as shown below:

Column 7, line 32: "alkyl or" should read --alkyl of--.

Signed and Sealed this

Eighth Day of November, 1988

Attest:

DONALD J. QUIGG

*Attesting Officer*     *Commissioner of Patents and Trademarks*